United States Patent [19]

Wright et al.

[11] Patent Number: 5,013,577
[45] Date of Patent: May 7, 1991

[54] SILOXANE SOLUBLE $(CH_3)_3SIO_{\frac{1}{2}}/SIO_2$ (M/Q) RESINS WITH AMINE AND AMIDE ORGANOFUNCTIONALITY

[75] Inventors: Antony P. Wright, Rhodes; Padmakumari J. Varaprath, Midland, both of Mich.

[73] Assignee: Dow Corning Corporation, Midland, Mich.

[21] Appl. No.: 570,668

[22] Filed: Aug. 22, 1990

[51] Int. Cl.$^5$ .............................................. B05D 3/06
[52] U.S. Cl. .......................................... 427/35; 528/38; 528/39; 525/477; 525/478; 525/474; 427/54.1
[58] Field of Search ..................... 528/39, 38; 525/477, 525/478, 474; 427/54.1, 35

[56] References Cited

U.S. PATENT DOCUMENTS

| | | | |
|---|---|---|---|
| 2,557,803 | 6/1951 | Sommer | 260/448.2 |
| 2,738,357 | 3/1956 | Speier | 260/448.2 |
| 2,754,312 | 7/1956 | Elliott | 260/448.2 |
| 2,762,823 | 9/1956 | Speier | 260/448.2 |
| 2,929,829 | 3/1960 | Morehouse | 260/448.2 |
| 2,998,406 | 8/1961 | Bailey et al. | 260/46.5 |
| 3,045,036 | 7/1962 | Kenmore et al. | 260/448.2 |
| 3,087,909 | 4/1963 | Morehouse et al. | 260/46.5 |
| 3,355,424 | 11/1967 | Brown | 260/46.5 |
| 3,560,543 | 2/1971 | Pleuddemann | 260/448.2 |
| 3,890,269 | 6/1975 | Martin | 260/46.5 |
| 4,036,868 | 7/1977 | Atherton | 260/448.2 |
| 4,152,346 | 5/1979 | Seiler et al. | 260/448.2 |
| 4,507,455 | 3/1985 | Taugney et al. | 528/26 |
| 4,526,955 | 7/1985 | Bennington et al. | 525/477 |
| 4,591,622 | 5/1986 | Blizzard et al. | 525/477 |
| 4,608,270 | 8/1986 | Varaprath | 427/35 |

Primary Examiner—Melvyn I. Marquis
Assistant Examiner—M. Glass
Attorney, Agent, or Firm—Killworth, Gottman, Hagan & Schaeff

[57] ABSTRACT

Organosilicon amine capped resins are prepared by reacting silanol siloxane resins with a cyclic silazane. The product organosilicon amine capped resins are reacted with an acyl halide to yield siloxane resins with amide organofunctionality. The later reaction is especially useful for obtaining acrylamide organofunctionality which is polymerizable and useful in formulating coating compositions such as pressure sensitive adhesives.

40 Claims, No Drawings

SILOXANE SOLUBLE $(CH_3)_3SiO_{\frac{1}{2}}/SiO_2$ (M/Q) RESINS WITH AMINE AND AMIDE ORGANOFUNCTIONALITY

BACKGROUND OF THE INVENTION

This invention relates generally to a method for preparing organosilicon amine and amide capped resins and to the organosilicon amine and amide capped resins obtained thereby. More specifically, the method involves the reaction of a silozane resin containing silanol groups with a cyclic silazane to give a silicon-capped siloxane resin containing amino functionality and the reaction of the amino functionality with an acyl halide to yield a siloxane resin with amide organofunctionality.

Aminosilicon compounds are well known in the organosilicon art as exemplified by U.S. Pat. Nos. 2,557,803, 2,738,357, 2,754,312, 2,762,823, 2,998,406, 3,045,036, 3,087,909, 3,355,424, 3,560,543, 3,890,269, 4,036,868, 3,355,424, 4,507,455. The silylation of hydroxyl groups in siloxane resins as an endcapping process also is well known in organic synthesis and occurs effectively with silazanes, silylamines, acetoxysilanes, acetamidosilanes and oximosilanes. However, in none of the methods known for preparing aminosilicon compounds or silylating siloxane hydroxyl groups is a silanol group capped with the silylating moiety while at the same time introducing an amino group into the compound.

Organosilicon compounds that contain silicon-bonded acylamino-substituted hydrocarbon radicals are well known and have been described in U.S. Pat. No. 4,608,270 to Varaprath, which is herein incorporated by reference.

As mentioned in Varaprath U.S. Pat. No. 4,608,270 and as taught in U.S. Pat. No. 2,929,829 to Morehouse, Japan 51/108022 to Furuya et al., Japan 56/74113 to Takamizawa, and West German DE 2365272 to Koetzsch et al., acylaminoorganopolysiloxanes can be synthesized by reacting aminosiloxanes with the corresponding acid chloride in the presence of a tertiary amine such as triethylamine. However, such a synthesis has several disadvantages. First, the removal of the voluminous precipitate of triethylamine hydrochloride by filtration is tedious. Second, a small amount of HCl is liberated even when an excess of amine is used. This HCl is detrimental to the stability of the polymer especially when the acid chloride has other reactive vinyl functionality such as where the acid chloride is an acrylyl chloride.

An alternative method for the preparation for the acylaminoorganopolysiloxanes involves the reaction of aminosiloxanes and silanes with an acid anhydride or ester at elevated temperature. This is taught in U.S. Pat. No. 4,507,455 to Tangney and Ziemelis, assigned to the assignee of the present invention. Unfortunately at the elevated temperatures of the reaction, acrylamide derivatives undergo Michael additional and amidation of the acrylic double bond resulting in unwanted by-products and crosslinkage of the desired product which ultimately causes the polymer to gel.

Finally as taught in the above-mentioned U.S. Pat. No. 4,608,270 to Varaprath, these problems can be overcome by reacting the aminosilanes and siloxanes with acid chlorides in the presence of aqueous sodium hydroxide. The HCl that is produced on addition of acyl chloride is neutralized by hydroxide in the aqueous phase.

BRIEF SUMMARY OF THE INVENTION

By silylating the hydroxyl groups of a siloxane resin with a cyclic silazane, the hydroxyl groups of the resin are capped by the silicon moiety of the silazane while simultaneously introducing amine functionality onto the siloxane resin. Such an endcapped amino functional resin is useful in formulating silicon-containing emulsifiers and other similar products.

The endcapped amine functional resin can be converted to acylamide functionality by the process detailed in U.S. Pat. No. 4,608,270 to Varaprath or in copending application Ser. No. 336,938, filed Apr. 10, 1989, now U.S. Pat. No. 4,889,942, to Guteck and Wright, both of which are hereby incorporated by reference. When the resulting acylamide functional resin is an acrylyl or methacrylylamide that is curable by, for example, electron beam, ultraviolet radiation, or free-radical means, it can be used for a wide range of applications including use in UV cure release coatings, as a reinforcing resin in UV conformal coatings, as a high-release additive in paper coatings especially when combined with organic additives, and to make radiation-cure pressure-sensitive adhesives. The amine functional resin can also be mixed with an aminofunctional fluid and converted to acylamide by the Varaprath process described in U.S. Pat. No. 4,608,270 or Ser. No. 336,938.

The amine-capped siloxane resins of this invention are of general formula $((CH_3)_3SiO_{\frac{1}{2}})_x(SiO_2)_y(O_{3/2}SiOY_2SiQNHB)_z$, where the ratio of "x" to "y"+"x" is within the range of 0.6/1.0 to 1.2/1.0; the ratio of "z" to "y" is within the range 0.01/1.0 to 0.4/1.0; Y is a monovalent organic radical or a hydrogen atom; Q is a divalent organic radical; and B is a hydrogen atom, a monovalent hydrocarbon radical (R), or an amino radical having the formula —Q'NZE where Q' is a divalent organic radical, Z is a hydrogen atom or a monovalent hydrocarbon radical (R), and E is a hydrogen atom or a monovalent hydrocarbon radical (R'). Q can be the same or different than Q'; R can be the same or different than R'. Preferably the ratio of "x" to "y+z" is about 1.0/1.0; the ratio of "z" to "y" is about 0.24/1.00; Y is a methyl radical; Q is an isobutylene radical; and B is a methyl radical or hydrogen atom. When B is the amino radical —Q'NZE, preferably Q' is an ethylene radical and Z and E are both hydrogen atoms. More preferably the formula of the amine-capped compounds of this invention is $((CH_3)_3SiO_{\frac{1}{2}})_{38}(O_{3/2}SiO(CH_3)_2SiCH_2CH(CH_3)CH_2NHCH_3)_{12}$.

The amide-capped siloxane resins of this invention are of general formula $((CH_3)_3SiO_{\frac{1}{2}})_x(SiO_2)_y(O_{3/2}SiOY_2SiQNAG)_z$, where the ratio of "x" to "y"+"z" is within the range of about 0.6/1.0 to about 1.2/1.0; the ratio of "z" to "y" is within the range of about 0.01/1.0 to about 0.4/1.0; Y is a monovalent organic radical R or a hydrogen atom; Q is a divalent organic radical; A is an acyl radical; and G is a hydrogen atom, a monovalent hydrocarbon radical, an amine radical having the formula —Q'NRR' where Q', R and R' are as defined above, or an amide radical having the formula —Q'-NZ$_a$A$_b$ where Q', A and Z are as defined above, "a"+"b" is 2 and "a" is 0 or 1. Preferably the ratio of "x" to "y+z" is about 1.0/1.0; the ratio of "z" to "y" is about 0.24/1.00; Y is a methyl radical; Q is an isobutylene radical; G is a methyl radical; and A is an acrylyl or methacrylyl radical. More preferably the formula of the amide-capped compounds of this invention is $((CH_3)_3SiO_{\frac{1}{2}})_{38}(SiO_2)_{50}(O_{3/2}SiO(CH_3)_2SiCH_2CH(CH_3)CH_2N(CH_3)COCH=CH_2)_{12}$.

The amine-capped siloxane resins are prepared by reacting the silanol groups of a siloxane resin composed of $(CH_3)_3SiO_{\frac{1}{2}}$ units, $SiO_2$ units, and $HOSiO_{3/2}$ units in which the ratio of $(CH_3)_3SiO_{\frac{1}{2}}$ units to $SiO_2$ and $HOSiO_{3/2}$ units is within a range from 0.6/1.0 to 1.2/1.0 and the ratio of $HOSiO_{3/2}$ units to $SiO_2$ units is within a range from 0.01/1.0 to 0.4/1.0 within a cylic silazane of the formula

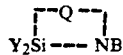

where Y is a monovalent organic radical or a hydrogen atom, Q is a divalent radical, and B is a hydrogen atom, a monovalent hydrocarbon radical, or an amino radical having the formula —Q'NZE where Q', Z and E are as defined above. Preferably the ratio of $(CH_3)_3SiO_{\frac{1}{2}}$ units to $SiO_2$ and $HOSiO_{3/2}$ units in the silanol/siloxane resin is about 1.0/1.0; the ratio of $HOSiO_{3/2}$ units to $SiO_2$ units is about 0.32/1.00; Y is a methyl radical; Q is an isobutylene radical; and B is a methyl radical or a hydrogen atom. When B is the amino radical —Q'NZE, preferably Q' is an ethylene radical and Z and E are hydrogen atoms. Most preferably the silanol/siloxane resin is of the formula: $((CH_3)_3SiO_{\frac{1}{2}})_{38}(SiO_2)_{50}(O_{3/2}SiOH)_{12}$ and the silazane is of the formula

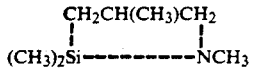

Typically the amine functional resin is prepared by reacting the silanol/siloxane resin with the cyclic silazane for a few hours under a nitrogen atmosphere at reflux temperatures. The reaction is very rapid in the presence of trifluoroacetic acid but trifluoroacetic acid is not required in all cases. A solvent is not required but a nonreactive solvent may be used to dilute the reactants and products.

The amide functional resin is prepared by reacting the above described amine functional resin with an acyl halide. Typically the amine functional resin is diluted with a nonreactive solvent and added to an aqueous solution of an alkali metal hydroxide. The acyl halide is added at room temperature. When the acyl halide is in acrylyl halide, the mixture is cooled to about 0° C. after which acrylyl halide is added slowly with mixing. The organic phase containing the amide functional resin is separated from the aqueous phase and the organic solvent is removed using, for example, a rotary evaporator.

The amino functional resin may also be combined with amino functional polydimethylsiloxane fluids such as aminoethylaminoisobutylpolydimethylsiloxane. The amino functionality of both the resin and fluid is converted to acrylamide functionality for use as radiation curable release coatings, pressure sensitive adhesives, or as conformal coatings. Preferably, for ultraviolet light cure, a polymerization initiator such as a free radical generator, e.g., a photoinitiator, is added to the curable composition to facilitate curing. A cured silicon-containing coating is obtained by applying a curable coating composition containing acrylamide functionality to a substrate and then curing the coating by a free radical process or with an electron beam or ultraviolet radiation.

DETAILED DESCRIPTION OF THE PREFERRED EMBODIMENTS

The amine-capped siloxane resins of this invention are of general formula $((CH_3)_3SiO_{1/2})_x—(SiO_2)_y(O_{3/2}SiOY_2SiQNHB)_z$, where the ratio of "x" to "y"+"z" is within the range of 0.6/1.0 to 1.2/1.0; the ratio of "x" to "y" is within the range 0.01/1.0 to 0.4/1.0. Preferably the ratio of "x" to "y"+"z" is about 1.0/1.0 and the ratio of "z" to "y" is about 0.24/1.00.

The terminal "Y" radicals on the silicon include monovalent organic radicals such as alkyl radicals such as methyl (Me), ethyl (Et), propyl, butyl, hexyl, and octyl; cycloaliphatic radicals such as cyclohexyl; aryl radicals such as phenyl (Ph), benzyl, styryl (cinnamenyl, i.e. PhCH=CH—), tolyl, and xenyl; and alkenyl radicals such as vinyl and allyl and halogenated derivatives thereof, alkoxy radicals such as methoxy and ethoxy radicals, aryloxy radicals, and hydrogen atoms.

Preferably monovalent organic radicals containing no more than 6 carbon atoms, such as methyl, 3, 3, 3 trifluoropropyl, phenyl and vinyl radicals and, most preferably, methyl radicals are used.

The divalent organic Q radical, which links the silicon and nitrogen atoms, includes, but is not limited to, alkylene radicals such as —$CH_2CH_2$—, —$CH_2CH_2CH_2$—, —$CH_2CH(CH_3)CH_2$—, —$(CH_2)_6$— and

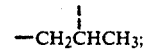

oxy radicals such as —$OCH(CH)_3CH_2$—; and arylene radicals such as —$C_6H_4$—, —$CH_2C_6H_4$—, and —$CH_2C_6H_4CH_2$—. Preferably Q is an isobutylene radical.

The terminal B group on the nitrogen atom includes a hydrogen atom, a monovalent hydrocarbon radical (R), or an amino radical having the formula —Q'NZE.

In the amino radical —Q'NZE, the divalent organic Q' radical, which links the two nitrogen atoms, includes, but is not limited to, alkylene radicals such as —$CH_2CH_2$—, —$CH_2CH_2CH_2$—,

—$CH_2CHCH_3$, and —$(CH_2)_6$—; $OCH(CH)_3CH_2$—; and arylene radicals such as —$C_6H_4$—, —$CH_2C_6H_4$—, and —$CH_2C_6H_4CH_2$—. Preferably Q is an isobutylene radical. Q' can be the same as or different than Q. Preferably Q' is an ethylene radical.

The terminal Z group can be a hydrogen atom or a monovalent hydrocarbon radical R. The terminal E group can be a hydrogen atom or a monovalent hydrocarbon radical R'. The terminal Z group can be the same as or different than the terminal E group.

The terminal monovalent hydrocarbon radicals R and R' include, but are not limited to, alkyl radicals such as methyl, ethyl, propyl, butyl, hexyl, and octyl; cycloaliphatic radicals such as cyclohexyl; aryl radicals such as phenyl, benzyl, styryl (cinnamenyl), tolyl, and xenyl; and alkenyl radicals such as vinyl and allyl. Preferably R or R' is a methyl radical. More preferably the formula of the amine-capped compounds of this invention is $((CH_3)_3SiO_{\frac{1}{2}})_{38}(SiO_2)_{50}-(O_{3/2}SiO(CH_3)_2SiCH_2CH(CH_3)CH_2NHCH_3)_{12}$.

The amide-capped siloxane resins of this invention are of general formula $((CH_3)_3SiO_{\frac{1}{2}})_x(SiO_2)_y(O_{3/2}SiOY_2SiQNAG)_z$, where the ratio of "x" to "y"+"z" is within the range of 0.6/1.0 to 1.2/1.0; the ratio of "z" to "y" is within the range 0.01/1.0 to 4.0/1.0. Preferably the ratio of "x" to "y"+"z" is about 1.0/1.0 and the ratio of "z" to "y" 0 is about 0.32/1.00.

In the compounds of this invention, A denotes an acyl radical having the formula

R″CO where R″ includes, but is not limited to, a substituted or unsubstituted monovalent hydrocarbon radical bonded to the carbonyl group. Examples of unsubstituted acyl R″ group hydrocarbon radicals include, but are not limited to, monovalent radicals such as alkyl radicals such as methyl, ethyl, propyl, butyl, hexyl, and octyl; cycloaliphatic radicals such as cyclohexyl; aryl radicals such as phenyl, benzyl, styryl (cinnamenyl), tolyl, and xenyl; and alkenyl radicals such as vinyl, isopropenyl and allyl. Examples of substituted acyl R″ group hydrocarbon radicals include, but are not limited to, halogenated R radicals such as $-CF_3$ and $-C_6H_4Cl$, and other substituted radicals which are stable under the reaction conditions employed in the method of this invention such as $-CH_2CH_2CN$, $-C_6H_4NO_2$ and $-C(CN)=CH_2$. Preferably R″ is an acrylyl or methacrylyl radical.

The terminal G group of this invention may be a hydrogen atom, a terminal monovalent hydrocarbon radical R, a tertiary amine group having the formula $-Q'NRR'$, or an amide group having the formula $-Q'NZ_aA_b$ where "a"+"b" is 2 and "a" is 0 or 1. The Y, Q, Q', Z, R, and R' groups are the same as those given above for the amine-capped siloxane resins. Most preferably the formula of the acrylamide-capped siloxane resin of this invention is $((CH_3)_3SiO_{178})_{38}(SiO_2)_{50}(O_{3/2}SiO(CH_3)_2SiCH_2CH(CH_3)CH_2N(CH_3)COCH=CH_2)_{12}$.

The amine-capped siloxane resins are prepared by reacting the silanol groups of a siloxane resin composed of $(CH_3)_3SiO_{\frac{1}{2}}$ units, $SiO_2$ units, and $HOSiO_{3/2}$ units in which the ratio of $(CH_3)_3SiO_{\frac{1}{2}}$ units to $SiO_2$ and $HOSiO_{3/2}$ units is within a range from about 0.6/1.0 to about 1.2/1.0 and the ratio of $HOSiO_{3/2}$ units to $SiO_2$ units is within a range from about 0.01/1.0 to about 0.4/1.0 with a cyclic silazane of the formula

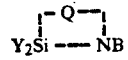
$Y_2Si---NB$ where Y is a monovalent organic radical or a hydrogen atom, B is a hydrogen atom, a terminal monovalent hydrocarbon radical (R), or an amino radical having the formula $-Q'NZE$ where Q' is a divalent organic radical, Z is a hydrogen atom or a hydrocarbon radical (R), and E is a hydrogen atom or a hydrocarbon radical R'. Examples of Y, Q, Q' R, and R' are given above. Preferably the ratio of $(CH_3)_3SiO_{\frac{1}{2}}$ units to $SiO_2$ and $HOSiO_{3/2}$ units in the silanol/siloxane resin is about 1.0/1.0; the ratio of $HOSiO_{3/2}$ units to $SiO_2$ units is about 0.24/1.00; Y is a methyl radical; Q is an isobutylene radical; and B is a methyl radical or a hydrogen atom. When B is the amino radical-QNZE, preferably Q is an ethylene radical and Z and E are hydrogen atoms. Most preferably the silanol/siloxane resin is of the formula: $((CH_3)_3SiO_{\frac{1}{2}})_{38}(SiO_2)_{50}(O_{3/2}SiOH)_{12}$ and the silazane is of the formula:

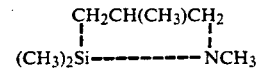

Typically the amine functional resin is prepared by reacting the silanol/siloxane resin with the cyclic silazane for a few hours under a nitrogen atmosphere at reflux temperatures in the presence of trifluoroacetic acid. Trifluoroacetic acid is not required in all cases. A solvent is not required but a nonreactive solvent may be used to dilute the reactants and products.

In the method of this invention, the acyl halide is added to the aminosilicon resin in the presence of an aqueous solution of an alkaline material. The alkaline material can be any water-soluble material having a pKb value greater than the pKb of the amine radicals in the amino-substituted hydrocarbon radicals to be acylated. The alkaline material is preferably an alkali metal hydroxide such as sodium hydroxide or potassium hydroxide.

In addition to the aqueous solution of alkaline material, there is also present a water-insoluble solvent for the aminosilicon resin when the acyl halide is admixed to the aminosilicon compound. Said solvent can be any suitable liquid that will not react with the components of the reaction. Preferably the solvent is also a solvent for the organosilicon product of the reaction as well.

Examples of suitable solvents include, but are not limited to, hydrocarbons such as toluene, xylene, hexane, cyclohexane and heptane; halogenated hydrocarbons such as methylene chloride, chloroform, trichloroethylene and trichloroethane; and oxygenated compounds such as ethyl ether and ethyl acetate. Mixtures of two or more solvents can also be used, it only being required in this instance that the mixture, and not necessarily all the components in the mixture, be a solvent for the aminosilicon compound.

In the method of this invention, the necessary components of the reaction mixture, i.e. the acyl halide, the aminosilicon resin, the aqueous solution of alkaline material and solvent, can be mixed in any manner as long as the acyl halide is added to the aminosilicon resin in the presence of the other two necessary components. In a preferred embodiment the acyl halide, or a solution thereof, is added to a well agitated mixture of the aqueous alkaline material and solvent solution of aminosilicon resin.

Except when the acyl halide is an acrylyl halide the method of this invention can be practiced at any reasonable temperature. Advantageously this method proceeds readily at room temperature. When an acrylyl halide is used this method should be practiced at as low a temperature as possible to minimize the formation of byproducts. Accordingly, when using the method of this invention to prepare acrylyl-substituted aminosilicon resins, the reaction should be conducted at a temperature of from about 0° to about 10° C. Lower reaction temperatures are appropriate provided the water does not freeze, but higher reaction temperatures will substantially reduce the yield of desired product.

The amounts of the necessary components to be used in this method are not narrowly critical, it only being necessary to have present a sufficient amount of alkaline material to neutralize all hydrogen halide as it is produced when the acyl halide reacts with the nitrogen-bonded hydrogen atoms and a sufficient amount of acyl halide to acylate every molecule of aminosilicon compounds at least once.

Thus the alkaline material and the acyl halide are preferably used in equivalent amounts; e.g. one molecule of sodium hydroxide for every molecule of acyl chloride, although an excess of the alkaline material reactive to the amount of hydrogen halide produced has not been found to be detrimental to the desired result of the reaction. A deficiency of alkaline material relative to the amount of hydrogen halide produced is to be avoided.

Also, the acyl halide and the aminosilicon resin should be used in equivalent amounts; e.g. one acyl chloride molecule for every molecule of aminosilicon compound which bears an acylatable amino group, although an excess of the acyl halide relative to acylatable amino groups has not been found to be detrimental to the desired result of the reaction. A deficiency of acyl halide, relative to the total number of acylatable amino groups, although merely leading to the preparation of incompletely acylated product when the acyl halide is free of aliphatic unsaturation, leads to products which can undergo a Michael-Addition type reaction when the acyl halide contains aliphatic unsaturation. For this reason it is preferred, although not required, to fully acrylate the aminosilicon compound when an acrylyl halide is used.

The amount of water that is used in the method of this invention should be sufficient to dissolve the alkaline material and, preferably, provide a less-than-saturated solution thereof. A 2% solution of sodium hydroxide has been found to be desirable.

The amount of solvent that is used in the method of this invention should be sufficient to dissolve the aminosilicon resin, and, preferably, the amidesilicon product as well.

During and after the addition of the acyl halide component to the aminosilicon component the reaction mixture should be thoroughly agitated to maintain an intimate contact between the aqueous and nonaqueous phases. The usual low shear means such as stirrers, paddles and impellers are sufficient to maintain sufficient agitation. Agitation is maintained until the acylation reaction is finished, typically within an hour.

After the reaction is finished and the organic phase has been isolated, the product of the reaction can be separated from the solvent or allowed to remain in the solvent as desired. When acrylyl-substituted products are to be separated from the solvent, it is desirable to add a polymerization inhibitor to the solution prior to any separating action such as distilling or fractioning.

The products of the method of this invention are useful as polar silicon-containing additives for cosmetic compositions, coating compositions, textile treating compositions and paints. The compositions of this invention are useful as comonomers with polymerizable vinyl monomers such as styrene, butadiene, methyl methacrylate, ethyl acrylate, vinyl acetate, vinyl chloride, vinylidene chloride and acrylonitrile. In particular, the compounds of this invention bearing acrylylamine-substituted hydrocarbon radicals are useful as a reactive component in free radical curable compositions such as radiation curable compositions.

The aminofunctional resin may also be combined with amino functional polydimethylsiloxane fluids such as aminoethylaminoisobutylpolydimethylsiloxane. The amino functionality of both the resin and fluid is converted to acrylamide functionality for use as radiation curable release coatings, pressure sensitive adhesives, or as conformal coatings. Preferably, a polymerization initiator such as a free radical generator or a photoinitiator is added to the curable composition to facilitate curing. A cured silicon-containing coating is obtained by applying a curable coating composition containing acrylamide functionality to a substrate and then curing the coating by a free radical process or with an electron beam or ultraviolet radiation.

This invention also relates to curable coating compositions containing acrylamide-capped siloxane resins of the formula $((CH_3)_3SiO_{\frac{1}{2}})_x(SiO_2)_y-(O_{3/2}SiY_2SiQNJG)_z$, wherein the ratio of the "x" to "y"+"z" is within the range of 0.6/1.0 to 1.2/1.0; the ratio of "z" to "y" is within the range 0.01/1.0 to 0.4/1.0; Y is an organic radical or a hydrogen atom; Q is a divalent organic radical; J is an acrylyl group, e.g., an alpha, beta unsaturated carbonyl radical such as an acrylyl or methacrylyl radical; and the terminal G group is a hydrogen atom, a terminal monovalent hydrocarbon radical R, a tertiary amine group having the formula —Q'NRR', or an amide group having the formula —Q'NZ$_a$A$_b$ where "a"+"b" is 2 and "a" is 0 or 1. The Y, Q, Q', Z, R, and R' groups are the same as those given above for the amine-capped siloxane resins. Preferably, the ratio of "x" to "y"+"z" is about 1.0/1.0, the ratio of "z" to "y" is about 0.32/1.00, Y is a methyl radical, Q is an isobutylene radical, G is a methyl radical and J is an acrylyl or methacrylyl radical.

In particular, curable compositions of this invention which are useful for coating a flexible substrate such as paper, polymer films and metal foils should comprise, as the acrylated silicon compound, a fully acrylated siloxane having the formula $((CH_3)_3SiO_{\frac{1}{2}})_{38}(SiO_2)_{50}(O_{3/2}SI(CH_3)_2SiCH_2CH(CH_3)CH_2N(CH_3)COCH=CH_2)_{12}$.

The curable compositions of this invention consist of a fully acrylated silicon resin, with or without the addition of curing agents. However, it is preferable to include therein a polymerization initiator such as a free radical generator to facilitate the curing thereof when the composition is to be cured by thermal and/or ultraviolet radiation. The particular initiator to be included depends upon the method to be used for curing the composition.

When the composition is to be cured by thermal means, it is preferred that a free radical initiator be added to the curable composition. Examples of suitable free radical initiators include, but are not limited to, redox pairs, perborates, percarbonates, photochemical systems, azo compounds such as benzoyl peroxide, alkyl peroxides such as di-t-butyl peroxide and hydroperoxides such as cumene hydroperoxide.

When the composition is to be cured by ultraviolet radiation it is preferred that a photoinitiator be added to the composition. Examples of suitable photoinitiators include, but are not limited to, benzoin, benzoin alkyl ethers such as methyl, ethyl, isopropyl or isobutyl benzoin ether, acetophenone derivatives such as dialkoxyacetophenone such as diethoxyacetophenone, di- and trichloroacetophenones, alpha, alpha-dimethoxy-alphaphenylacetophenone, 1-hydroxycyclohexylphenyl ketone, 2-hydroxy-2-methyl-1- phenyl-propane-1-one, methylphenyl glyoxylate, 4- benzoyl-benzyl-trimethylammonium chloride, alpha-acyloxime esters such as 1-phenyl-1, 2- propandedione-2-(O-ethoxycarbonyloxime), thioxanthane and its derivatives, benzophenone in combination with a chain transfer agent such as a NH group and azo-bis(isobutyronitrile).

The reader is referred to any of the standard references that teach the polymerization of acrylyl-containing monomers, such as the Kirk-Othmer Encyclopedia of Chemistry and Technology; John Wiley and Sons, N.J., Second Edition, 1972, Vol. I, pp. 274 to 284 or the *Encyclopedia of Polymer Science and Technology*; John Wiley and Sons, N.J., 1966, Vol. I, pp. 177 to 197, for further details.

When the curable compositions of this invention are to be cured by electron beam radiation the addition of a polymerization initiator is not needed.

The curable compositions of this invention can further comprise optional components which are commonly used in curable silicon-containing compositions. Examples of said optional components include, but are not limited to, solvents such as those used to prepare the acrylated silicon resin used therein, polymerizable vinyl monomers such as styrene, butadiene, methyl methacrylate, ethyl acrylate, vinyl acetate, vinyl chloride, and acrylonitrile, emulsion-forming components such as water and surfactant, colorants, stabilizers, fillers such as silica and carbon, adhesion promoters, and surface modifiers such as lubricants and release agents.

The curable coating compositions of this invention thus have many of the utilities of curable compositions such as molding, encapsulating, sealing and coating. In particular they find utility for coating flexible substrates such as paper, metal foil, polymer films, optical fibers and textiles and relatively non-flexible substrates such as polymer laminates such as circuit boards, siliceous substrates and molded, cast and stamped metal articles. The curable coatings of this invention are useful int he adhesives release art, the electronic art such as encapsulating and photoresist, the graphic art, etc.

In another aspect, the present invention relates to a process providing a cured silicon-containing coating on a substrate by applying the curable coating composition of this invention to the substrate and thereafter curing the applied coating.

The curable coating composition of this invention is applied to a substrate as a thin layer by any suitable manner such as brushing, spraying, rolling, dipping or spreading. By a thin layer it is meant form a monomolecular layer to a hundred mils. Curable coating compositions of this invention comprising siloxane compounds of this invention are typically applied in a layer having a thickness of from 0.01 to 100 mils.

The applied coating can be cured by any suitable means such as chemical, radiant or thermal means. As noted above, when the applied coating is to be cured by thermal or ultraviolet radiation, the applied composition should contain a polymerization initiator. In a preferred embodiment of this invention, the applied composition is cured with electron beam radiation and the composition needs no added initiator.

As noted above, the coating composition of this invention can be applied to substrates of various compositions, shapes, sizes and uses. In a preferred embodiment of this process, a flexible substrate is coated for the purpose of providing for the substrate an adhesive-releasing surface.

In the adhesive-releasing art, a flexible substrate such as paper, polymer film, polymer-coated paper or metal foil is rendered adhesive-releasing by the application of a curable fluid composition to the flexible substrate at a coating weight of from 0.5 to 2 pounds per ream of substrate. After the applied composition has been cured, the thus-treated surface is brought into adhesive contact with an adhesive, either free or disposed on a surface of an article. The adhesive-releasing surface thereby serves as a protective layer for one surface of the adhesive until the adhesive is to be used, whereupon it can be readily removed from the adhesive.

In the process of this invention there is provided a fast, clean, efficient process for providing an adhesive-releasing surface that is fully cured, non-transferring and stable when used with cast adhesives or supported adhesives and in an on-line, i.e. immediate adhesive coating, mode or in a conversion, i.e. delayed adhesive coating, mode.

The following examples are disclosed to further teach how to practice the invention in its several aspects and not to limit the invention which is properly delineated by the appended claims.

TABLE I

| COMPOSITION | Release Coatings | | |
|---|---|---|---|
| | A | B | C |
| ACRYLAMIDE RESIN | | | |
| Weight (grams) | 7.0 | 7.0 | — |
| ACRYLAMIDE POLYMER | | | |
| Weight (grams) | 3.0 | 3.0 | 10.0 |
| DP | 75 | 75 | 75 |
| Mole % | 5.0 | 5.0 | 5.0 |
| Pendant | x | x | x |
| 1,6 HEXANEDIOL-DIACRYLATE | — | 5.0% | 5.0% |
| Radiation Dose (megarads) | 4-6 | 4-6 | 4-6 |
| Oxygen (ppm) | 230 | 210 | 220 |
| RELEASE FORCE (gm/inch) | | | |
| Adhesive | Age (days) | Delamination | | | |
| SBR | 1 | 400 in/min | 50 | 42 | 18 |
| SBR | 7 | 400 in/min | 21 | 19 | 13 |
| SBR | 30 | 400 in/min | 19 | 37 | 13 |
| Acrylic | 1 | 400 in/min | — | 62 | 27 |
| | | 0 in/min | — | 401 | 116 |
| | | 12 in/min | — | 353 | 89 |
| | | 78 in/min | — | 167 | 57 |
| | | 10 m/min | — | 74 | 41 |
| | | 100 m/min | — | — | 32 |
| Acrylic | 7 | 400 in/min | — | 56 | 25 |
| Acrylic | 30 | 400 in/min | — | 35 | 68 |

TABLE II

| COMPOSITION | Release Coatings | | | | | | | | | | | |
|---|---|---|---|---|---|---|---|---|---|---|---|---|
| | A | B | C | D | E | F | G | H | I | J | K | L |
| ACRYLAMIDE RESIN | | | | | | | | | | | | |
| Weight (grams) | — | 7.0 | 7.0 | 7.0 | — | 7.0 | 7.0 | 7.0 | — | 7.0 | 7.0 | 7.0 |
| ACRYLAMIDE POLYMER | | | | | | | | | | | | |
| Weight (grams) | 10.0 | 3.0 | 3.0 | 3.0 | 10.0 | 3.0 | 3.0 | 3.0 | 10.0 | 3.0 | 3.0 | 3.0 |
| DP | 75 | 75 | 75 | 87 | 75 | 75 | 75 | 75 | 75 | 75 | 75 | 75 |

TABLE II-continued

| COMPOSITION | Release Coatings | | | | | | | | | | | |
|---|---|---|---|---|---|---|---|---|---|---|---|---|
| | A | B | C | D | E | F | G | H | I | J | K | L |
| Mole % | 5.0 | 5.0 | 5.0 | 5.0 | 5.0 | 5.0 | 5.0 | 5.0 | 5.0 | 5.0 | 5.0 | 5.0 |
| Pendant | X | X | X | X | X | X | X | X | X | X | X | X |
| 1,6 HEXANEDIOL-DIACRYLATE (HDDA) Ratio Resin/Polymer:HDDA | 10:2 | 10:1 | 10:2 | 10:3 | — | — | — | — | — | — | — | — |
| ISOBUTOXYACRYLAMIDE (IBAA) Ratio Resin/Polymer:IBAA | — | — | — | — | 10:2 | 10:1 | 10:2 | 10:3 | — | — | — | — |
| N-VINYL PYRROLIDONE (NVP) Ratio Resin/Polymer:NVP | — | — | — | — | — | — | — | — | 10:2 | 10:1 | 10:2 | 10.3 |
| Radiation Dose (megarads) | 5 | 4 | 6 | 4 | 4 | 4 | 4 | 4 | 4 | 4 | 4 | 4 |
| Oxygen (ppm) | 200 | 240 | 210 | 200 | 200 | 200 | 200 | 200 | 180 | 200 | 200 | 180 |

RELEASE FORCE (gm/inch)

| Adhesive | Age (days) | Delamination | | | | | | | | | | | |
|---|---|---|---|---|---|---|---|---|---|---|---|---|---|
| SBR | 1 | 400 in/min | 30 | 40 | 24 | 28 | 32 | 54 | 34 | weld | 28 | 28 | 41 | 31 |
| SBR | 7 | 400 in/min | 22 | 13 | 18 | 18 | 42 | 34 | 26 | 43 | 20 | 23 | 36 | 23 |
| SBR | 30 | 400 in/min | 30 | 42 | 34 | 33 | 50 | 46 | 42 | weld | 21 | 30 | 45 | 33 |
| | 0 | 400 in/min | 31 | 192 | 225 | 106 | 132 | 235 | 117 | — | 29 | 230 | 228 | 192 |
| | | 12 in/min | 40 | 27 | 33 | 12 | 71 | 81 | 65 | weld | 21 | 78 | 74 | 57 |
| | | 78 in/min | 22 | 27 | 20 | 11 | 49 | 23 | 17 | weld | 16 | 24 | 40 | 17 |
| | | 10 in/min | 29 | 26 | 32 | 32 | 56 | 59 | 42 | weld | 21 | 36 | 50 | 30 |
| | | 100 in/min | 22 | 19 | 20 | 16 | 21 | 24 | 42 | weld | 15 | 24 | 21 | 17 |

TABLE III

| PRESSURE SENSITIVE ADHESIVE | ACRYLAMIDE RESIN POLYMER | CURED FILM TACKINESS | LAP SHEAR DAYS TO FAIL |
|---|---|---|---|
| 100% | 0% | Tacky (poor cure) | <<1 |
| 80% | 20% | Tacky | <<1 |
| 60% | 40% | Tacky | +1 (pass) |
| 40% | 60% | Non-tacky | — |
| 20% | 80% | Non-tacky | — |

EXAMPLE I

Two hundred fifty grams of a silanol/siloxane resin with 66% solids were refluxed under a nitrogen blanket in a three-neck one liter flask equipped with a stirrer, thermometer and Dean Stark trap at 145° C. for 30 minutes to remove any traces of water. After cooling to 25° C., 28.0 g of 1, 2, 2, 4 tetramethyl-1-aza-2-silacyclopentane and 4 drops of trifluoroacetic acid were added. The mixture was allowed to react at 130° C. for 3 hours yielding an amino resin with a nonvolatile content of 74%.

The amino resin (100.1 g) was mixed with 87 g of a 50 DP, 4 mole % pendant aminoethylaminoisobutyl-polydimethylsiloxane (PDMS) fluid and the xylene stripped off at 75° C. and 10 torr pressure. The amino resin polymer had a viscosity of 723 cs and an amine neutral equivalent of 1038.55 g per mole amine as determined by perchloric acid titration in glacial acetic acid using methyl violet as an indicator. The ratio of amino resin to polymer was calculated to be 46:54 parts by weight.

The amine functionality of the amino resin polymer was converted to acrylamide functionality by diluting 60 g of the amino resin polymer with 200 ml of trichloroethylene, cooling the flask to −5° C., adding 60 g water containing 2.8 g sodium hydroxide pellets, adding 5 ml of acrylyl chloride slowly over 10 minutes, phase separating, adding 0.5 ml para-methoxyhydroquinone inhibitor, 1 ml of tetrahydrofuran, and stripping the organic phase on a rotary evaporator to yield an acrylamide resin polymer having a viscosity of over 10,000 cs. The addition of acrylamide was repeated using hydroquinone as a polymerization inhibitor but the viscosity was unchanged.

The acrylamide resin polymer, 2.5 parts, was mixed with 7.5 parts 50 DP 5 mole % pendant acrylamide functional PDMS. This was coated on a polyethylene coated paper at 1.2 lbs per ream and cured under 3 megarad electron beam dose in an atmosphere containing 250 ppm oxygen. Then the cured film was coated with a 3 mil layer of adhesive using either a dispersion of styrene-butadiene rubber adhesive (SBR adhesive; National Starch; New York, N.Y.; 36-6045) or acrylic adhesive (Monsanto; St. Louis, MO; GMS 263) in heptane, dried 1 minute at 70° C., laminated to 60 lb matte litho label stock, and delaminated 24 hours later at 400 inches per minute, the release force was between 100 and 127 grams per inch test strip width, even after 30 days aging at 25° C. thus demonstrating that the material is curable in a thin film and acts as a pressure sensitive adhesive release coating.

EXAMPLE II

Two hundred fifty grams of a silanol/siloxane resin analyzing at 4.43 wt % hydroxyl with 66% solids in xylene and an additional 30 ml xylene were refluxed under a nitrogen blanket in a three-neck one liter flask equipped with a stirrer, thermometer and Dean Stark trap at 145° C. for 30 minutes to remove any traces of water. After cooling to 70° C., 28.3 g of 1, 2, 2, 4 tetramethyl-1- aza-2- silacyclopentane and 4 drops of trifluoroacetic acid were added. The mixture was allowed to react at 130° C. for 3 hours yielding an amino resin with a nonvolatile content of 73%, a hydroxyl content of 0.85% and an amine neutral equivalent of 1431.58.

To demonstrate that the amine present was not due merely to the dimerization of 1, 2, 2, 4 tetramethyl-1-aza-2- silacyclopentane to the disoloxane according to the reaction sequence:

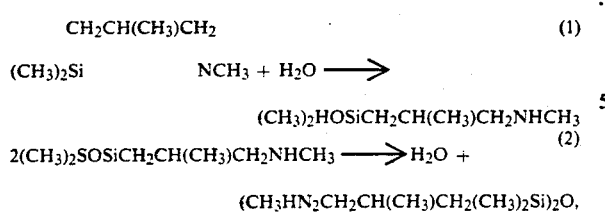

$$(CH_3)_2Si\begin{matrix}CH_2CH(CH_3)CH_2\\ \\NCH_3\end{matrix} + H_2O \longrightarrow \quad (1)$$

$$(CH_3)_2HOSiCH_2CH(CH_3)CH_2NHCH_3 \quad (2)$$

$$2(CH_3)_2SOSiCH_2CH(CH_3)CH_2NHCH_3 \longrightarrow H_2O +$$

$$(CH_3HN_2CH_2CH(CH_3)CH_2(CH_3)_2Si)_2O,$$

2.0 g of the disiloxane was found to completely evaporate from an aluminum pan heated at 150° C. for 1.5 hours. When the amino resin was heated on an aluminum pan at 150° C. for 3 hours and then the amine neutral equivalent redetermined based on the original weight of the amino resin, the amine neutral equivalent was found to have increased from 1431.58 to 1693.12 showing that less than 15% of the amine could have been disiloxane or lower boiling components and demonstrating that most of the amine had capped the silanol/siloxane resin.

One hundred grams of the amino resin was mixed with 89 grams of a 75 DP, 5 mole % pendant aminoethylaminoisobutyl PDMS fluid and the xylene stripped off at 150° C. and 5 torr pressure. The amine neutral equivalent was 914.4 grams per mole amine by perchloric acid titration in glacial acetic acid using methyl violet as an indicator. The ratio of resin to polymer was calculated to be 46:54 parts by weight.

The amine resin polymer mixture was converted to acrylamide by diluting 40 g of the mixture with 120 ml trichloroethylene, cooling the solution to 0° C., adding 100 g water containing 2.23 g sodium hydroxide pellets, adding 4.34 acrylyl chloride slowly over 7 minutes, phase separating, adding 0.4 ml hydroquinone inhibitor solution (made by dissolving 0.5 g hydroquinone in 50 ml ethanol), 2 ml ethanol, and stripping the organic phase on a rotary evaporator for one hour to yield an acrylamide resin polymer with a viscosity of 68,280 cs.

The acrylamide resin polymer was mixed with various amounts of 75 DP, 5 mole % acrylamide polymer and occasionally 5% 1, 6 hexanediol-di-acrylate. The compositions were coated on paper as in Example I and cured with 4-6 megarads of electron beam radiation. The compositions were laminated with SBR or acrylic adhesive and release forces were measured at various times and delamination speeds. No significant differences were observed when the resin polymer was used alone or with the acrylamide polymer unless 1, 6-hexanedioldiacrylate was present. As seen in Table I, release forces were much higher when the resin was combined with 1, 6- hexanedioldiacrylate then when the resin was not present. Thus under certain conditions, the resin can act as a high release additive.

EXAMPLE III

The acrylamide resin/polymer was prepared from the amine resin polymer according to the method given in Example II. Seventy parts of the acrylamide resin/polymer was mixed with 30 parts 75 DP 5 mole % fluid 6638-122,123. As a control, the resin free fluid was also used alone. To 10 parts of this mixture or control fluid were added 1, 2, or 3 parts each of 1, 6-hexanedioldiacrylate (HDDA), isobutoxyacrylamide (IBAA), or N-vinyl pyrrolidone (NVP) and tested according to the method give in Examples 1 and 2 with the results presented in Table II. These results show little trend in release forces at 10 meters/minute or higher. At lower speeds, HDDA and NVP (Compositions A and L, respectively) showed no increase in force if the acrylamide resin/polymer was not present. However, with the resin present, the release forces were higher (Compositions B, C, D, I, J and K). With IBAA, the release forces were increased even if no resin was present (Composition E) but were much more so if the resin/polymer were also present (Compositions F, G and H).

EXAMPLE IV

An amino resin polymer and an acrylamide resin polymer were prepared according to the procedure described in Example I but using a lower molecular weight silanol siloxane resin polymer. The amino resin polymer had a viscosity of 220 cs while the acrylamide resin polymer had a viscosity of 4637 cs. The acrylamide resin polymer was curable by electron beam radiation.

EXAMPLE V

An amine resin polymer was made by combining 53 parts by weight of silanol siloxane resin solids, 47 parts of a hydroxy terminated polydimethylsiloxane gum of a molecular weight of about 600,000, 150 parts xylene and 2.8 parts water with about 5 parts of 1, 2, 2, 4 tetramethyl-1-aza-2-silacyclopentane per 100 parts of the above solution and about three drops of trifluoroacetic acid and refluxing the mixture for three hours. The product had an amine neutral equivalent of 2500 and a solids content of 55%. The silanol content was negligible demonstrating that amine capping was complete. The amine resin polymer was reacted with acrylyl chloride to yield the acrylamide resin polymer by dissolving 67 g of the amine resin polymer in 250 ml chloroform, cooling to 0° C., and adding 1.54 g sodium hydroxide dissolved in 60 ml of water at 0° C. followed by acrylyl chloride. The mixture was stirred five minutes at 0° C. and then poured into a separatory funnel. The organic layer was then separated, dried over anhydrous sodium sulfate, filtered, and most of the solvent removed to obtain the acrylamide functional pressure sensitive adhesive. The acrylamide resin polymer was mixed with 4% Irgacure 500 (Ciba Geigy), coated on mylar followed by evaporation of the remaining solvent, and cured by passing under two 200 watt/in UV lamps at 60 ft/minute in air. The cured film was non-tacky indicating that although a satisfactory radiation set bonding adhesive had been successfully made, a tacky pressure sensitive adhesive had not been achieved.

A new amine functional resin polymer was made by the same method but using less 1, 2, 2, 4 tetramethyl-1-aza-2-silacyclopentane. The amine neutral equivalent was 5000. This was converted to the acrylamide resin polymer and cured as before to a non-tackey film. When the acrylamide resin polymer was mixed with various amounts of a conventional resin/gum based silicone pressure sensitive adhesive, 4% Irgacure 500 photoinitiator added, and UV cured on mylar film; the results shown in Table III were obtained. Table III shows that a mixture of 60 parts of resin/gum based silicone pressure sensitive adhesive and 40 parts of acrylamide resin polymer give the correct crosslink density to form a radiation cure pressure sensitive adhesive. The uncured film was too soft to display any lap shear strength.

What is claimed is:

1. An amine-capped siloxane resin of the formula $((CH_3)_3SiO_{\frac{1}{2}})_x(SiO_2)_y(O_{3/2}SiOY_2SiQNHB)_z$ wherein the ratio of "x" to the sum of "y"+"z" is within the range of about 0.6/1.0 to about 1.2/1.0;

the ratio of "z" to "y" is within the range from about 0.01/1.0 to about 0.4/1.0;

Y is a monovalent organic radical or a hydrogen atom;

Q is a divalent organic radical; and

B is a hydrogen atom,
a monovalent hydrocarbon radical R or
an amino radical having the formula —Q'NZE wherein
Q' is a divalent organic radical the same or different than Q,
Z is a hydrogen atom or a monovalent hydrocarbon radical R, and
E is a hydrogen atom or a monovalent radical R' the same or different than R.

2. The amine-capped siloxane resin according to claim 1 wherein the ratio of "x" to the sum of "y"+"z" is about 1.0/1.0.

3. The amine-capped siloxane resin according to claim 1 wherein the ratio of "z" to "y" is about 0.24/1.00.

4. The amine-capped siloxane resin according to claim 1 wherein Y is amethyl radical.

5. The amine-capped siloxane resin according to claim 1 wherein Q is an isobutylene radical.

6. The amine-capped siloxane resin according to claim 1 wherein B is a methyl radical or a hydrogen atom.

7. The amine-capped siloxane resin according to claim 1 wherein B is a —Q'NZE amino radical wherein Q' is an ethylene radical, Z is a hydrogen atom and E is a hydrogen atom.

8. The amine-capped siloxane resin according to claim 1 of the formula $((CH_3)_3SiO_{\frac{1}{2}})_{38}(SiO_2)_{50}$—$(O_{3/2}SiO(CH_3)_2SiCH_2CH(CH_3)CH_2NHCH_3)_{12}$.

9. A method for preparing an amine-capped siloxane resin, said method comprising reacting silanol groups of a siloxane resin composed of $(CH_3)_3SiO_{\frac{1}{2}}$ units, $SiO_2$ units, and $HOSiO_{3/2}$ units in which the ratio of $(CH_3)_3SiO_{\frac{1}{2}}$ units to the sum of $SiO_2$ and $HOSiO_{3/2}$ units is within a range from about 0.6/1.0 to about 1.2/1.0 and the ratio of $HOSiO_{3/2}$ units to $SiO_2$ units is within a range from about 0.01/1.0 to about 0.4/1.0 within a cyclic silazane of the formula

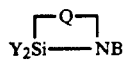

wherein
Y is a monovalent organic radical or a hydrogen atom,
Q is a divalent organic radical, and
B is a hydrogen atom,
a monovalent hydrocarbon radical R or
an amino radical having the formula
—Q'NZE wherein
Q' is a divalent organic radical the same or different than Q,
Z is a hydrogen atom or a monovalent hydrocarbon radical R and
E is a hydrogen atom or a monovalent hydrocarbon radical R' the same or different than R.

10. The method for preparing an amine-capped siloxane resin according to claim 9 wherein the ratio of $(CH_3)_3SiO_{\frac{1}{2}}$ units to the sum of $SiO_2$ and $HOSiO_{3/2}$ units in said siloxane resin is about 1.0/1.0.

11. The method for preparing an amine-capped siloxane resin according to claim 9 wherein the ratio of $HOSiO_{3/2}$ units to $SiO_2$ units in said siloxane resin is about 0.24/1.00.

12. The method for preparing an amine-capped siloxane resin according to claim 9 wherein Y of said cyclic silazane is a methyl radical.

13. The method for preparing an amine-capped siloxane resin according to claim 9 wherein Q of said cyclic silazane is an isobutylene radical.

14. The method for preparing an amine-capped siloxane resin according to claim 9 wherein B is a methyl radical or a hydrogen atom.

15. The method for preparing an amine-capped siloxane resin according to claim 9 wherein
B is an amino group of the formula —Q'NZE wherein
Q' is an ethylene radical,
Z is a hydrogen atom and
E is a hydrogen atom.

16. The method for preparing an amine-capped siloxane resin according to claim 9 wherein said siloxane resin is of the formula $((CH_3)_3SiO_{\frac{1}{2}})_{38}(SiO_2)_{50}(O_{3/2}SiOH)_{12}$.

17. The method for preparing an amine-capped siloxane resin according to claim 9 wherein said silaxane is of the formula:

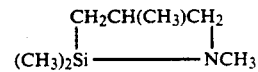

18. The method for preparing an amine-capped siloxane resin according to claim 9 wherein said reacting is carried out in the presence of trifluoroacetic acid.

19. An amide-capped siloxane resin of the formula $((CH_3)_3SiO_{\frac{1}{2}})_x(SiO_2)_y(O_{3/2}SiOY_2SiQNAG)_z$ wherein
the ratio of "x" to the sum of "y"+"z" is within the range of about 0.6/1.0 to about 1.2/1.0;
the ratio of "z" to "y" is within the range from about 0.01/1.0 to about 0.4/1.0;
Y is a monovalent organic radical or a hydrogen atom;
Q is a divalent organic radical;
A is an acyl radical having the formula

wherein
R″ is a substituted or unsubstituted monovalent hydrocarbon radical bonded to the carbonyl group;
G is a hydrogen atom,
a monovalent hydrocarbon radical,
an amine radical having the formula —Q'NRR' wherein R and R' are the same or different monovalent hydrocarbon radicals or
an amide radical having the formula —Q'NZ$_a$A$_b$ wherein
Q' is a divalent hydrocarbon radical the same or different from Q,
Z is a hydrogen atom or a monovalent hydrocarbon radical R previously defined,
A is an acyl radical previously defined, "a"+"b" is 2 and
"a" is 0 or 1.

20. The amide-capped siloxane resin according to claim 19 wherein the ratio of "x" to the sum of "y"+"z" is about 1.0/1.0.

21. The amide-capped siloxane resin according to claim 19 wherein the ratio of "z" to "y" is about 0.24/1.00.

22. The amide-capped siloxane resin according to claim 19 wherein Y is a methyl radical.

23. The amide-capped siloxane resin according to claim 19 wherein Q is an isobutylene radical.

24. The amide-capped siloxane resin according to claim 19 wherein G is a methyl radical.

25. The amide-capped siloxane resin according to claim 19 wherein A is an acrylyl or methacrylyl radical.

26. The amide-capped siloxane resin according to claim 19 of the formula $((CH_3)_3SiO_{\frac{1}{2}})_{38}(SiO_2)_{50}-(O_{3/2}SiO(CH_3)_2SiCH_2CH(CH_3)CH_2N(CH_3)COCH=CH_2)_{12}$.

27. A curable coating composition comprising an acrylamide-capped siloxane resin of the formula $((CH_3)_3SiO_{\frac{1}{2}})_x(SiO_2)_y(O_{3/2}SiOY_2SiQNJG)_z$ wherein the ratio of "x" to "y"+"z" is within the range of about 0.6/1.0 to about 1.2/1.0;

the ratio of "z" to "y" is within the range of about 0.01/1.0 to about 0.4/1.0;

Y is a monovalent organic radical or a hydrogen atom;

Q is a divalent organic radical;

J is an acrylyl group; and

G is a hydrogen atom, a monovalent hydrocarbon radical, an amine radical having the formula Q'NRR' wherein Q' is a divalent organic radical the same or different than Q and R and R' are the same or different monovalent hydrocarbon radicals or an amide radical having the formula $-Q'NZ_aJ_b$ wherein Q' is a divalent organic radical previously defined, Z is a hydrogen atom or a monovalent hydrocarbon radical R, J is an acrylyl group previously defined, "a+b" is 2 and "a" is 0 or 1.

28. The curable coating composition according to claim 27 wherein the ratio of "x" to "y"+"z" is about 1.0/1.0.

29. The curable coating composition according to claim 27 wherein the ratio of "z" to "y" is about 0.24/1.00.

30. The curable coating composition according to claim 27 wherein Y is a methyl radical.

31. The curable coating composition according to claim 27 wherein Q is an isobutylene radical.

32. The curable coating composition according to claim 27 wherein G is a methyl radical.

33. The curable coating composition according to claim 27 wherein J is an acrylyl or methacrylyl radical.

34. The curable coating composition according to claim 27 formula $((CH_3)_3SiO_{\frac{1}{2}})_{38}(SiO_2)_{50}(O_{3/2}SiO-(CH_3)_2SiCH_2CH(CH_3)CH_2N(CH_3)COCH=CH_2)_{12}$.

35. A process for providing a cured silicon-containing coating on a substrate using the curable coating composition of claim 27 comprising applying said curable coating composition to said substrate and curing said applied coating.

36. The process according to claim 35 wherein said curing is done by exposing the applied coating to a free radical generating means.

37. The process according to claim 35 wherein said curing is done by exposing the applied coating to electron beam radiation.

38. The process according to claim 35 wherein said curing is done by exposing the applied coating to ultraviolet radiation.

39. A curable coating composition according to claim 27 further comprising at least one polymerizable vinyl monomer.

40. A curable coating composition according to claim 39 further comprising at least one polymerization initiator.

* * * * *